(12) United States Patent
Cohn

(10) Patent No.: US 7,468,030 B1
(45) Date of Patent: Dec. 23, 2008

(54) SURGICAL RETRACTOR

(75) Inventor: William Cohn, Chestnut Hill, MA (US)

(73) Assignee: Beth Israel Deaconess Medical Center, Boston, MA (US)

(*) Notice: Subject to any disclaimer, the term of this patent is extended or adjusted under 35 U.S.C. 154(b) by 0 days.

(21) Appl. No.: 09/518,964

(22) Filed: Mar. 6, 2000

Related U.S. Application Data

(63) Continuation of application No. 09/307,195, filed on May 7, 1999, now Pat. No. 7,235,049, which is a continuation of application No. PCT/US98/08348, filed on Apr. 24, 1998, which is a continuation-in-part of application No. 08/845,333, filed on Apr. 25, 1997, now Pat. No. 6,033,362.

(51) Int. Cl.
*A61B 1/32* (2006.01)

(52) U.S. Cl. .................................................. 600/210

(58) Field of Classification Search ........ 600/201, 600/205, 209, 213, 233, 235, 211, 37, 210, 600/214, 217; 606/1
See application file for complete search history.

(56) References Cited

U.S. PATENT DOCUMENTS

| | | | |
|---|---|---|---|
| 3,983,863 A | 10/1976 | Janke et al. ................... 128/1 |
| 4,151,838 A | 5/1979 | Crew ............................ 128/20 |
| 4,366,819 A | 1/1983 | Kaster .......................... 128/334 |
| 4,368,736 A | 1/1983 | Kaster .......................... 128/334 |
| 4,461,284 A | 7/1984 | Fackler ......................... 128/20 |
| 4,622,955 A | 11/1986 | Fakhrai ........................ 128/20 |
| 4,637,377 A | 1/1987 | Loop ............................ 128/1 R |
| 4,726,356 A | 2/1988 | Santilli et al. ................. 128/20 |
| 4,973,300 A | 11/1990 | Wright ......................... 600/37 |
| 4,989,587 A | 2/1991 | Farley .......................... 128/20 |
| 5,088,472 A | 2/1992 | Fakhrai ........................ 128/20 |
| 5,150,706 A | 9/1992 | Cox et al. ..................... 128/400 |
| 5,167,223 A | 12/1992 | Koros et al. ................... 128/20 |
| 5,365,921 A | 11/1994 | Bookwalter et al. ........... 128/20 |
| 5,447,515 A | 9/1995 | Robicsek ...................... 606/158 |
| 5,452,733 A | 9/1995 | Sterman et al. ............... 128/898 |
| 5,501,698 A | 3/1996 | Roth et al. ..................... 606/205 |
| 5,509,890 A | 4/1996 | Kazama ........................ 600/37 |
| 5,569,274 A | 10/1996 | Rapacki et al. ............... 606/158 |

(Continued)

FOREIGN PATENT DOCUMENTS

CA 2216893 9/1997

(Continued)

OTHER PUBLICATIONS

Westaby, Stephen, "Coronary Surgery Without Cardiopulmonary Bypass", British Heart Journal, 1995.*

(Continued)

*Primary Examiner*—Jeffrey A. Smith
*Assistant Examiner*—Kalyan Deshpande
(74) *Attorney, Agent, or Firm*—Weingarten, Schurgin, Gagnebin & Lebovici LLP

(57) ABSTRACT

A present invention relates to a surgical retractor that immobilizes tissue at a surgical site. A preferred embodiment of the retractor is used during minimally invasive direct coronary bypass procedures to arrest movement of the grafting site while the heart continues pumping. Tape or thread can be used to connect the artery to the retractor with a holder.

35 Claims, 9 Drawing Sheets

U.S. PATENT DOCUMENTS

| | | | |
|---|---|---|---|
| 5,697,891 A | 12/1997 | Hori | 600/245 |
| 5,727,569 A | 3/1998 | Benetti et al. | 128/898 |
| 5,728,151 A | 3/1998 | Garrison et al. | 623/2 |
| 5,730,757 A * | 3/1998 | Benetti et al. | 600/214 X |
| 5,749,892 A * | 5/1998 | Vierra et al. | 600/201 X |
| D395,130 S | 6/1998 | Furnish | D24/135 |
| 5,769,870 A | 6/1998 | Salahieh et al. | 606/198 |
| 5,776,154 A | 7/1998 | Taylor et al. | 606/167 |
| 5,782,746 A | 7/1998 | Wright | 600/37 |
| 5,871,496 A | 2/1999 | Ginn et al. | 606/190 |
| 5,875,782 A | 3/1999 | Ferrari et al. | 128/898 |
| 5,876,332 A | 3/1999 | Looney | 600/227 |
| 5,888,247 A | 3/1999 | Benetti | 623/66 |
| 5,891,140 A | 4/1999 | Ginn et al. | 606/48 |
| 5,894,843 A * | 4/1999 | Benetti et al. | 128/898 |
| 5,957,835 A | 9/1999 | Anderson et al. | 600/201 |
| 6,001,111 A | 12/1999 | Sepetka et al. | 606/158 |
| 6,033,362 A | 3/2000 | Cohn | 600/213 |
| 6,036,641 A | 3/2000 | Taylor | 600/231 |
| 6,071,235 A | 6/2000 | Furnish et al. | 600/235 |
| 6,102,854 A | 8/2000 | Cartier et al. | 600/228 |
| 6,132,370 A | 10/2000 | Furnish et al. | 600/235 |
| 6,152,874 A | 11/2000 | Looney et al. | 600/214 |
| 6,254,535 B1 | 7/2001 | Furnish et al. | 600/213 |

FOREIGN PATENT DOCUMENTS

| | | |
|---|---|---|
| DE | 297 07 567 U1 | 4/1997 |
| DE | 297 08 050 U1 | 8/1997 |
| EP | 0 336 526 A1 | 10/1989 |
| EP | 0 356 410 A1 | 2/1990 |
| EP | 0 630 629 A1 | 12/1994 |
| EP | 0 668 058 A1 | 8/1995 |
| EP | 0 791 330 A2 | 8/1997 |
| EP | 0 808 606 A1 | 11/1997 |
| EP | 0 820 721 A1 | 1/1998 |
| FR | 1019217 | 1/1953 |
| WO | 87/04081 | 7/1987 |
| WO | 94/14383 | 7/1994 |
| WO | 95/15715 | 6/1995 |
| WO | 95/17127 | 6/1995 |
| WO | 96/04854 | 2/1996 |
| WO | 97/10753 | 3/1997 |
| WO | 97/20524 | 6/1997 |
| WO | 97/27807 | 8/1997 |
| WO | 98/25549 | 6/1998 |
| WO | WO 98/48703 | 11/1998 |
| WO | WO 98/48704 | 11/1998 |
| WO | 99/11201 | 3/1999 |
| WO | WO 99/09892 | 3/1999 |
| WO | WO 00/42936 | 7/2000 |

OTHER PUBLICATIONS

Borst, C. et al. Coronary Artery Bypass Grafting Without Cardiopulmonary Bypass and Without Interruption of Native Coronary Flow Using a Novel Anastromosis Site Restraining Device ("octopus"), *jacc*, 27(6) :1355-1364 (1996).

Cartier et al., "Triple Coronary Artery Revascularization on the Stabilized Beating Heart: Initial Experiance", *CJS*, 41(4) :283-288 (Aug. 1998).

Perrault, et al., "Snaring of the Target Vessel in Less Invasive Bypass Operations Does Not Cause Endothelial Dysfunction", *Ann Thorac Surg*, 63:751-755 (1997).

Favaloro et al., "Direct Myocardial Revascularization by Saphenous Vein Graft", *Ann Thorac Surg*, 10(2) :97-111 (Aug. 1970).

Stephen Westaby, Editorial, "Coronary Surgery Without Cardiopulmonary Bypass", *Br. Heart J.*, 73:203-205 (1995).

Cutler et al., "New Use for an Old Clamp", *Arch Surg.* 115:1136-1137, (Sep. 1980).

Roux et al., "Internal Mammary Artery Dissection: A Three Dimensional Sternal Retractor", *J. Cardiovasc Surg.*, 30:996-997 (1989).

Cremer et al., "Off-Bypass Coronary Bypass Grafting via Minithoracotomy Using Mechanical Epicardial Stabilization", *Ann Thorac Surg*, 63:S79-83 (1997).

Bonatti et al., "Single Coronary Artery Bypass grafting—A Comparison Between Minimally Invasive 'Off Pump' Techniques and Conventional Procedures", *Euro J Cardo-thorac Sur* 14(Suppl 1) :S7-S12 (1998).

Westaby et al., "Less Invasive Coronary Surgery: Consensus From the Oxford Meeting", *Ann Thorac Surg* 62:924-931 (1996).

Arom et al., "Mini-Sternotomy for Coronary Artery Bypass Grafting", *Ann Thorac Sur* 61:1271-1272 (1996).

D. Cooley, "Limited Access Myocardial Revascularization", *Texas Heart Ins. J.* 23(2) :81-84 (1996).

Editorial, *Ann Thorac Surg* 62:1883-1892 (1996).

Badellino et al., "The Cardiac Rag", *Simple Exposure to the Heart* 15(2) :114-135 (1988).

Kazama, et al., "Fabric Heart Retractor for Coronary Artery Bypass Operations", *Ann Thorac Surg* 55:1582-1583 (1993).

Calafiore et al., "Minimally Invasive Coronary Artery Bypass Grafting", *Ann Thorac Surg* 62:1545-1548 (1996).

Pittman, et al., "Improved Visualization of the Internal Mammary Artery With a New Retractor System", *Ann Thorac Surg* 48:869-870 (1989).

Ancalmo et al., "A Modified Sternal Retractor", *Dept. Surgery, Alton Ochsner Medical Foundation and Ochsner Clinic* p. 174 (1975).

Phillips et al., "A Versatile Retractor for use in Harvesting the Internal Mammary Artery and Performing Standard Cardiac Operations", *J. Thorac Cardiovasc Surg* 97:633-635 (1989).

Oschner et al., "Surgical Management of Diseased Intracavitary Coronary Arteries", *Ann Thorac Surg* 38(4) :356-362 (Oct. 1984).

G. Green, "Technique of Internal Mammary—Coronary Artery Anastomosis", *J. Thorac Cardiovasc Surg.* 78:455-459 (1979).

Parsonnet et al., "Graduated Probes for Coronary Bypass Surgery", 68(3) :424-427 (Sep. 1974).

McKeown et al., "A Modified Sternal Retractor for Exposure of the Internal Mammary Artery", *Soc Thorac Sur* (1980).

Chaux et al., "A New Concept in Sternal Retraction: Applications for Internal Mammary Artery Dissection and Valve Replacement Surgery", *Ann Thorac Surg* 42:473-474 (Oct. 1986).

Rousou et al., "Cardiac Retractor for Coronary Bypass Operations", *Ann Thorac Surg* 52:877-878 (1991).

DelRossi, "A New Retractor to Aid in Coronary Artery Surgery", *Ann Thorac Surg* 36(1) :101-102 (Jul. 1983).

Roux et al., "New Helper Instrument in Cardiac Surgery", *Ann Thorac Surg* 48:595-596 (1989).

F. Robicsek, "Aortic Sppon-Jaw Clamp for Aorto-Saphenous Vein Anastomosis", *J. Card Surg* 10:583-585 (1995).

Hasan et al., "Technique of Dissecting the Internal Mammary After Using the Moussalli Bar", *Eur J. Cardo-thorac Surg* 4:571-572 (1990).

Parsonnet et al., "Self-retraining Epicardial Retractor for Aortocoronary Bypass Surgery", *J. Thorac Cardio Surg* pp. 629-630 (1979).

M. Bugge, "A New Internal Mammary Artery Retractor", *Thorac. Cardio. Surg.* 38:316-317 (1990).

Angelini et al., "A Simple, Inexpensive Method of Heart Retraction During Coronary Artery Bypass Surgery", *Ann Thorac Surg* 46:246-247 (Aug. 1988).

Matsuura et al., "A New Device for Exposing the Circumflex Coronary Artery", *Ann Thorac Surg* 59:1249-1250 (1995).

Murata et al., "Revascularization of the Circumflex Coronary Artery—A New Instrument and A Technical Method", *Jap. J. Thorac. Surg.* 42(2) 115-119 (1989) English Summary.

S. Eguchi, "A special Retractor for Stabilizing the Heart During Circumflex Coronary Grafting", *Dept. Surg Niiagata Univ. Sch. Med.* pp. 39-40 (1987) English Summary.

M. Vigano et al., "Applicazione dell'archetto di divaricamento vasale in corso di chirurgia coronarica", *Min Cardioang* 23(6-7) : 369-371 (1975) English Summary.

A. Eguchi. "Heart Retractor for Use in Anastomosis in Coronary Artery By-Pass Surgery", *Jap. J. Thorac. Surg.* 40(1) :1-2 (1987) English Summary.

* cited by examiner

SURGICAL RETRACTOR

RELATED APPLICATIONS

This is a continuation application of U.S. Ser. No. 09/307,195 filed on May 7, 1999 now U.S. Pat. No. 7,235,049 which is a continuation application of International Application No. PCT/US98/08348, filed on Apr. 24, 1998 and designating the United States which is a continuation-in-part application of U.S. Ser. No. 08/845,333 filed on Apr. 25, 1997 now U.S. Pat. No. 6,033,362, the entire teachings of the above applications being incorporated herein by reference.

BACKGROUND OF THE INVENTION

Numerous devices have been used to position tissue at a surgical site to aid in the performing of surgical procedures. Retractors, for example, have been used to hold an artery in position during operations adjacent to the heart to prevent movement of the artery. This serves to minimize the risk of injury to the artery and adjacent tissue and can facilitate the desired anastomosis.

A recently developed procedure, referred to as the minimally invasive direct coronary artery bypass procedure, has been used to graft onto a coronary artery without cardiopulmonary bypass. This procedure involves the grafting of the left internal mammary artery (LIMA) onto the left anterior descending (LAD) or other artery. As this procedure does not require the use of a heart lung machine to oxygenate and pump blood, the morbidity and mortality associated with this procedure is substantially lower than previous bypass techniques. A problem associated with the minimally invasive procedure, however, is that while the heart continues to pump during the procedure, the motion of the heart can interfere with the surgeon's task of attaching the LIMA to the LAD. There is also a need to stop blood flow in the area of the graft to maintain a clear field of view and provide precise suture placement.

Two basic strategies have been employed to address the problem of operating on a moving site, one being the use of pharmacological agents to limit heart motion, and the other being mechanical, such as a two prong retractor that is pushed down against the heart on both sides of the artery, or alternatively, upward traction away from the moving heart by traction tape or suture thread. Both of these options, however, have problems associated with them. Both options are susceptible to some movement of the vessel grafting site. The use of pharmacological agents is undesirable and impairs circulatory function. Traction by compression of the heart against the spine does serve to immobilize the site but can compromise the ability of the heart to maintain circulation and result in hypotension. Upward traction can involve circumferential compression of the artery to occlude the artery and prevent blood flow, however upward traction that is sufficient to immobilize the site can cause injury, stenosis or occlusion of the vessel.

There is a continuing need however for improvement in devices and methods for retaining tissue at surgical sites to further reduce the risks associated with surgical procedures where the devices and methods are inexpensive, safe and reliable.

SUMMARY OF THE INVENTION

The present invention relates to a surgical retractor for immobilizing tissue at a surgical site and to a method of using the retractor during a surgical procedure. A preferred embodiment of the retractor includes a retaining element having an aperture that exposes the surgical site and a holder that is used to position tissue at the surgical site relative to the retaining element. A handle can be attached to or fabricated with the retaining element or platform so that the user can manipulate the position of the retractor as needed.

In a preferred embodiment of the invention a connector such as elastic tape or thread is used to position tissue at the surgical site within the retractor aperture and to prevent movement of the tissue during the procedure. The connecting cord, thread or tape also aids in the compression of the artery in a grafting procedure to occlude flow on one or both sides of the surgical site. The cord is attached to the holder on the retaining element. A preferred embodiment of the holder can be a plurality of slits or openings positioned on both sides of the retractor that receive and frictionally secure the cord on both sides of the aperture. In another preferred embodiment a mechanical fastener is used to grip both sides of the cord. The fastener can be a spring mounted valve, for example, that allows the user to adjust the tension in the cord.

A preferred embodiment of the invention comprises a retaining element or base having two sections that can be separated after the procedure is complete to permit removal of the retractor from under the grafted artery. Another preferred embodiment uses a side opening in the platform of the retractor that extends to the aperture so that the grafted artery slips through the side opening during removal. During minimally invasive direct coronary artery bypass operations, one or more surface sections of the retractor platform can be positioned against the inner surface or posterior aspect of one or both ribs adjacent to the surgical site. Thus, the size and geometry of the platform are selected to utilize the adjoining ribs where the upper surface of the platform frictionally engages the inner surface one or more ribs to hold the retractor in a fixed position. The retractor can be beneficial in any procedure where it is necessary to stabilize a surgical site. For example, the retractor can also be used for grafting onto the diagonal, right or other coronary arteries without altering the heart's pumping function.

The coronary arteries are about 1-2 mm in diameter, and the pumping heart can move these arteries over distances of several millimeters during each heartbeat. As the movement of even 1 or 2 millimeters can result in a displacement of the grafting site that can substantially interfere with effective anastomosis, it is desirable to restrain movement of the artery at the surgical site in any direction to less than 1 mm. The retractor of the present invention restrains movement in the plane of the base to less than 0.5 mm, and preferably less than 0.2 mm.

In a preferred embodiment of the invention, the handle or articulating arm that is secured to the platform can be held in position by the user, attached to a frame that is fixed around the operative site or simply clipped to a drape around the site.

When used in a minimally invasive coronary bypass procedure, the retractor is positioned to expose the left anterior descending (LAD) artery grafting site after incision, removal of the rib section and dissection of the left internal mammary artery (LIMA) from the chest wall. A pair of cords, for example, sialastic tape (i.e. a silicon elastomer) or suture thread, are passed through the myocardium at two locations flanking the artery grafting site with blunt needles. The four ends of the two cords are connected to the platform holder with sufficient tension to occlude blood flow on both sides of the operative site. The tapes compress the artery against the bottom surface of the platform while they hold the artery grafting site in a fixed position relative to the aperture. The coronary artery is opened longitudinally and the end of the mammary artery is sewn to the graft opening with multiple fine sutures. The cords are released, blood flow is restored and the anastomosis is inspected for hemostatis and other defects and the wound is closed.

The platform can include tabs or cord retainers that extend into the aperture to provide a surface against which the arteries can be compressed.

Figure 4:
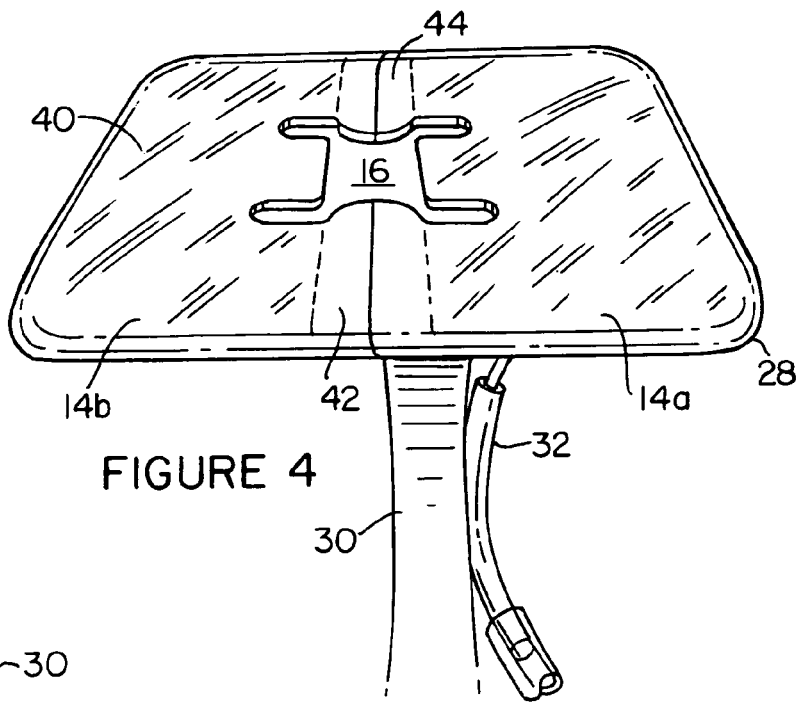
FIG. 4 is a bottom perspective view of a surgical retractor in accordance with the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
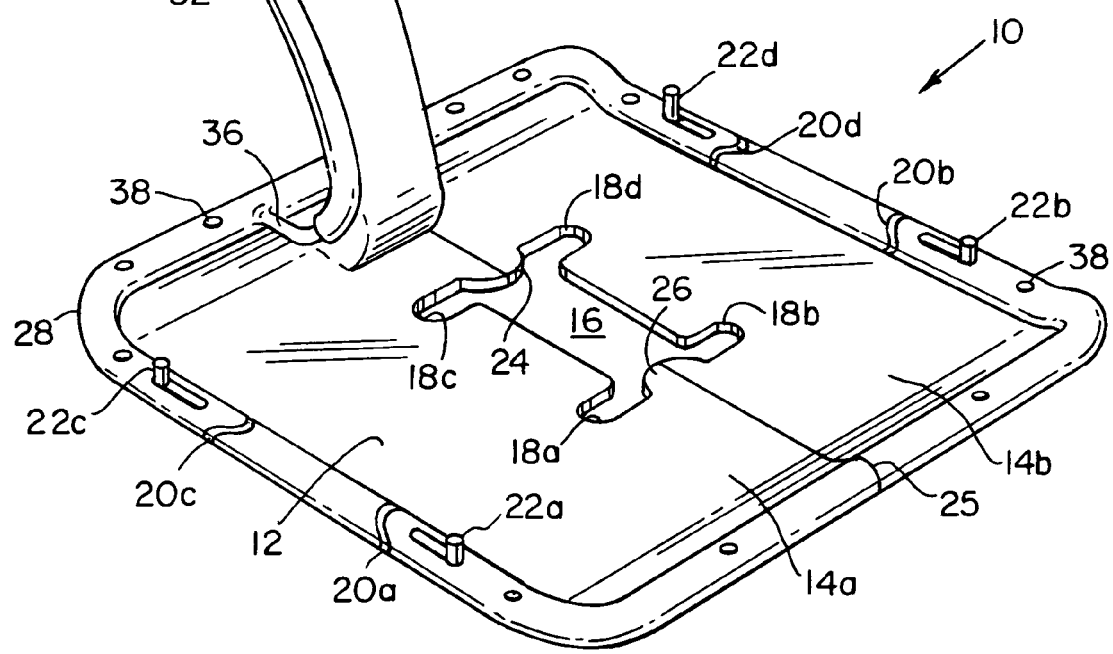
FIG. 1 is a perspective view of a surgical retractor in accordance with a preferred embodiment of the invention.

A preferred embodiment of the invention is illustrated in connection with FIG. 1. A retractor 10 includes a retaining element or base 12 having an aperture 16 that is positioned to expose tissue at a surgical site. The base 12 can be made with a metal or a molded plastic material. The retractor 10 can be sterilized after each use, or alternatively, can be disposable after one procedure. A handle 30 or articulating arm can be permanently attached to the base 12, or as described below in connection with other preferred embodiments, can be detachable.

A suction tube 32 can be attached to the handle 30 or integrated therein and is used to remove material such as blood from the operative site. In this particular embodiment the tube 32 is connected at one end to a tube 34 from a suction pump and connected at a second end to a port 36 in fluid communication with a channel within tube 28 that extends around the periphery of base 12. The peripheral tube can have small openings 38 positioned on the sides or top thereof through which fluid such as blood or other debris can be suctioned from the surgical site to maintain a clear field.

Figure 2:
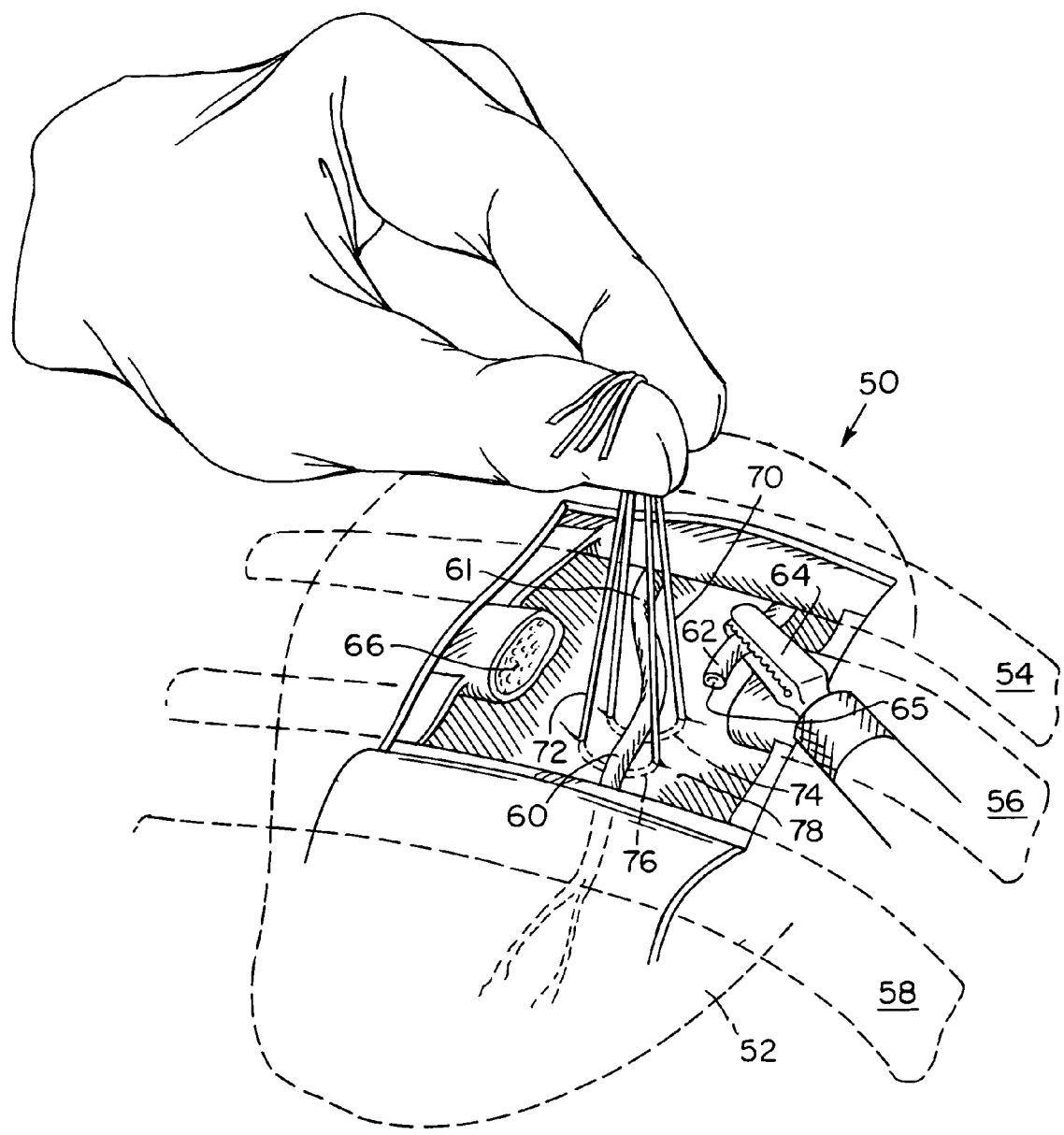
FIG. 2 is a perspective view of a surgical site illustrating a surgical procedure.

A preferred embodiment of the invention can be used at a surgical site 66 such as the example illustrated in FIG. 2. In this particular procedure for coronary graft without coardiopulmonary bypass, a section of the 4$^{th}$ costal cartilage or rib 56 is removed to expose a section of the LAD artery 61.

A proximal portion of the LIMA 62 is dissected from the chest wall to expose an end 65 to be grafted onto a grafting site 60 on artery 61. Blood flow in vessel 62 can be occluded with a clamp 64.

In this example, a connector such as a pair of cords or sialastic tapes 70, 72 are threaded through myocardium surface 78 under the artery 61 at two locations 74, 76 on opposite sides of the grafting site 60. Note that the exposed surface 78 of heart 52 is undergoing substantial movement during the procedure.

Figure 3:
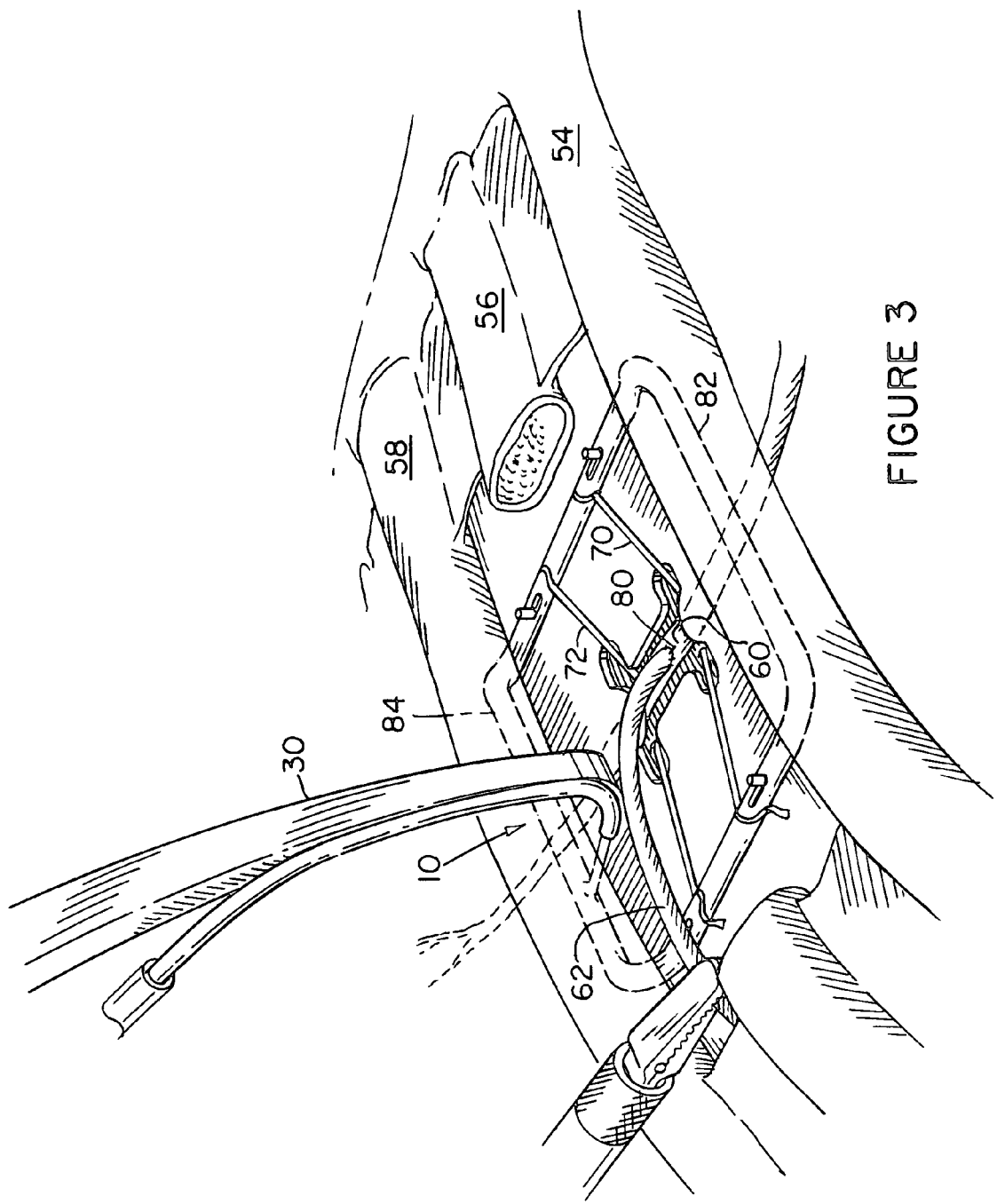
FIG. 3 is a perspective view of a surgical retractor for a grafting procedure in accordance with the invention.

As seen in the reverse perspective view of FIG. 3 in which the retractor 10 has been inserted and positioned during the procedure, the retractor 10 serves to immobilize the grafting site 60 using connecting tapes 70, 72 which are stretched and attached to a holder mechanism including slots 20a-20d in the peripheral edge of base 12. As described in greater detail below, the slots 20A-20d can be manually opened or closed using actuators 22a-22d, respectively, to allow the user to adjust the tension in the tapes or threads.

The aperture 16 extends longitudinally along the axis of artery 61. The site 60 is preferably located in the plane of the upper surface of base 12. The tapes 70, 72 exert a compressive force on the artery 61 which is pressed against a bottom surface 40 as seen in FIG. 4. More particularly, the tapes 70, 72 extend in a direction that is substantially perpendicular to the artery 61 axis exposed in the aperture 16. The aperture can have a first pair of lateral sections 18a and 18b which are aligned to accommodate the positioning of tape 70 and the aperture can also have a second pair of lateral sections 18c and 18d to accommodate the positioning of tape 72. Alternatively, holes extending through the base 12 that are separated from the aperture can be used. The holes are large enough to provide easy feed through and can be angled towards the bottom center to provide compression of the artery at lower tension of the cord.

The size of the aperture can be in the range of 1-3 cm in length and 5-15 mm in width. The aperture can be narrower in the center and wider at the opposite ends to accommodate the openings or sections 18a-18d.

Between each pair of sections 18a-18b and 18c-18d, a sidewall section of the aperture, namely tabs 24, 26 extend on opposite ends of aperture 16. The tapes 70, 72 compress respective portions of artery 61 on opposite sides of site 60 against tabs 26, 24. As seen in FIG. 4, those portions 42, 44 of the bottom surface 40 are in contact with artery 61 and compress it. The bottom surface that surrounds the artery and is in contact with the heart wall can be roughened or abraded to frictionally engage the heart wall around the artery and thereby locally restrict heart motion around the surgical site.

In a preferred embodiment of the invention opposite ends 82 and 84 can be positioned under adjacent ribs 54 and 58, respectively. This eliminates any substantial movement of the base 12 while the heart is pumping so that anastomosis 80 of the end 65 onto site 60 can be quickly completed. The opposite ends 82, 84 can be slightly raised relative to the plane of the remainder of the base 12 to provide a concave structure to enhance the frictional engagement of sections 82, 84 to ribs 54, 58, respectively. The platform has a substantially rectangular shape with each side having a length in the range between 3.5 cm and 6 cm. Thus the surface of the platform is between 12 cm$^2$ and 25 cm$^2$, preferably between 14 cm$^2$ and 20 cm$^2$. This size fits readily in the incision between the ribs and can be positioned with both ends extending under the 3rd and 5th ribs. This structure exerts little downward force on the heart or upward force on the artery while immobilizing the artery at the surgical site. Also the anterior-posterior compression of the artery avoids trauma to the artery due to circumferential compression. By engaging the ribs, the retractor is self-retaining providing for easier use and manipulation.

Figure 5:
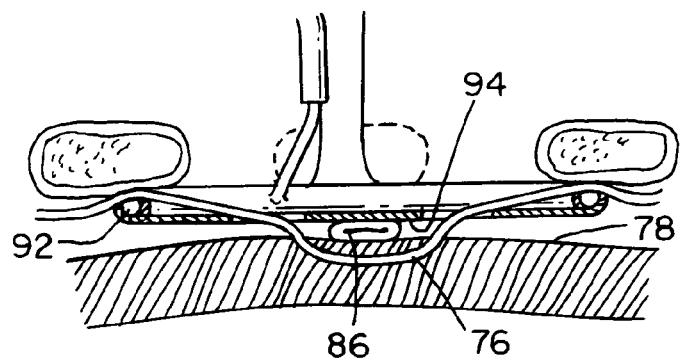
FIG. 5 is a cross-sectional view of a surgical retractor during a surgical procedure.

As seen in FIG. 5, the tape 76 under the bottom surface 94 of the tab 24 lifts the artery 60 to form an occlusion 86. This view also shows the optional channel 92 extending around the periphery of base 12 that is used to irrigate or suction around the site.

Figure 6A:
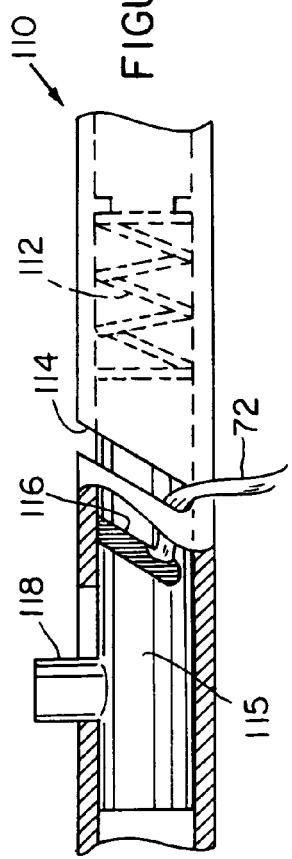
FIGS. 6A and 6B are partial cross-sectional views of a holder in accordance with the invention.
Figure 6B:
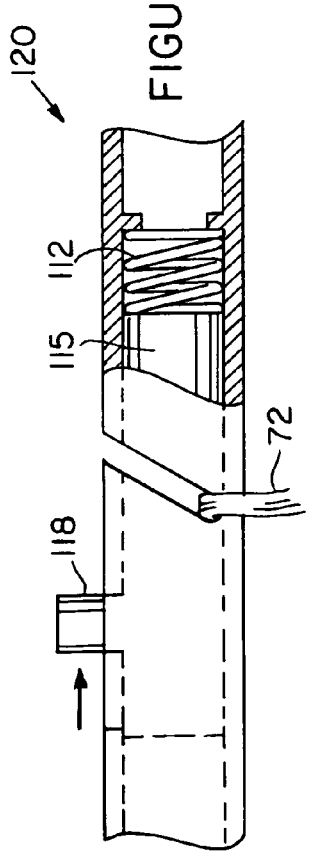

The fastening mechanism is illustrated in the partial cross-sectional views of FIGS. 6A and 6B. The closed position 110 is illustrated in FIG. 6A where spring 112 has expanded to move slot 116 in element 115 out of alignment with slot 114 in the outer tube. The cord 72 is displaced and frictionally grasped by the sliding movement of element 115. The user can manually displace 118 to align slot 114 with slot 116 while compressing spring 112. In the "open" position 120, the cord 72 can be easily removed or pulled through to increase tension.

Figure 7:
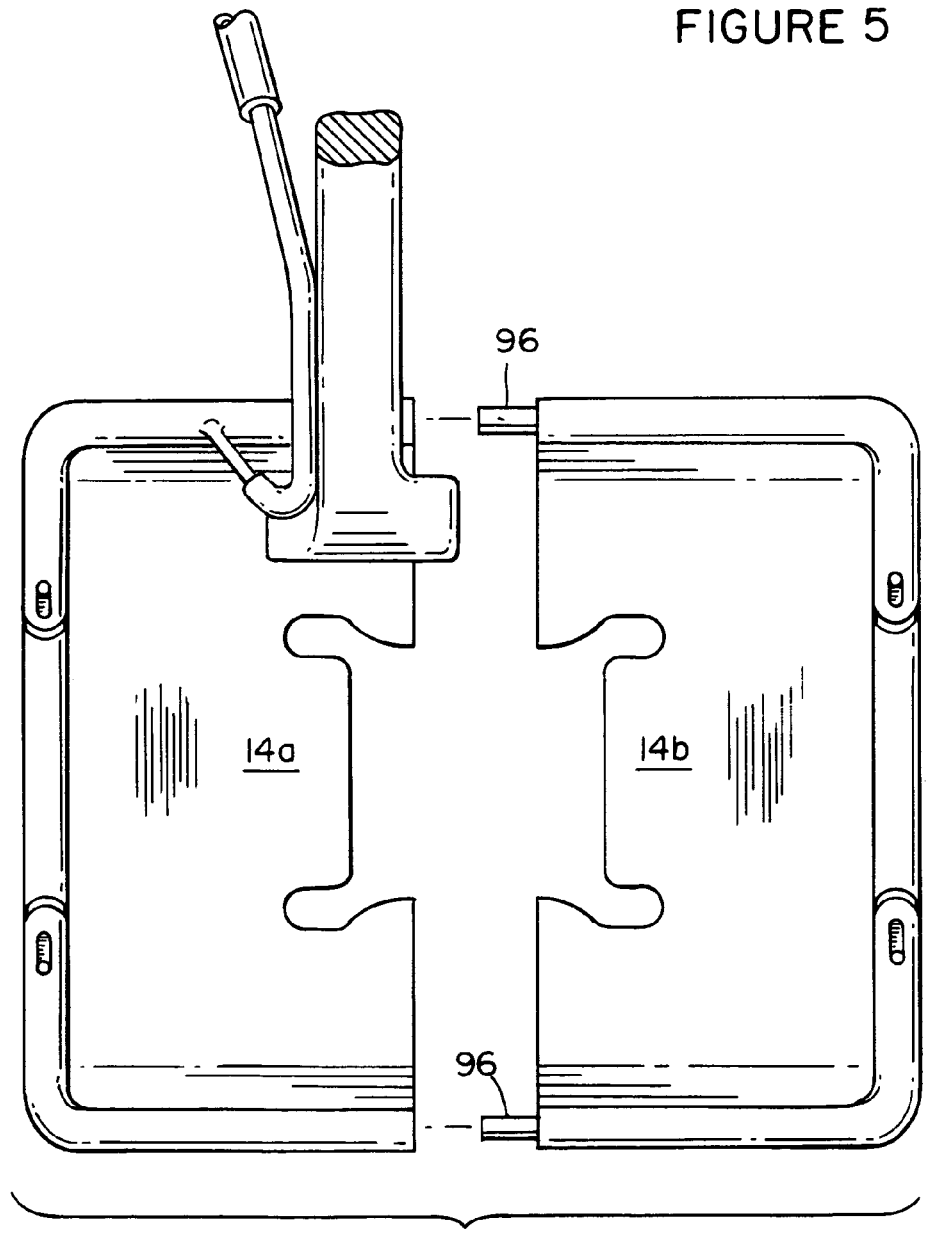
FIG. 7 is a top view of a two piece retainer in accordance with the invention.

After the procedure is complete the retractor 10 needs to be removed from the site. In the embodiment of FIG. 1, the base 12 can be formed with two sections or plates 14a, 14b. As seen in FIG. 7, these components can be separated at joint 25 to allow removal of the retractor 10. The two halves 14a, 14b can be connected with a frictional tube section 96.

Figure 8:
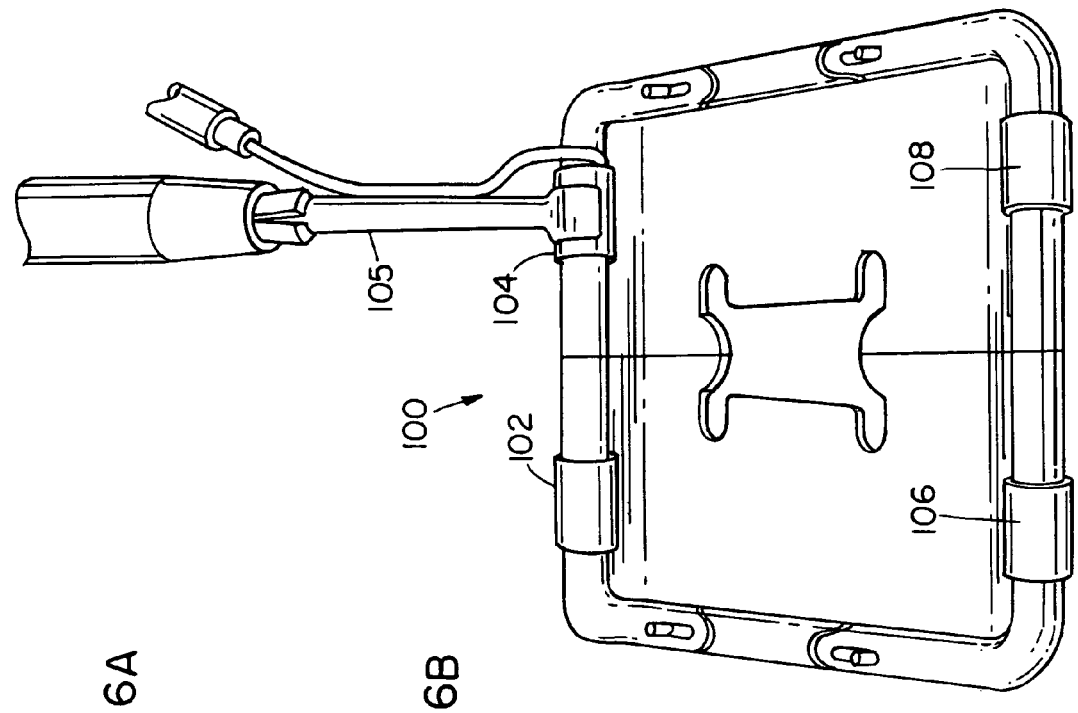
FIG. 8 is a top perspective view of another preferred embodiment of a surgical retractor in accordance with the invention.

In the preferred embodiment illustrated in FIG. 8, the retractor 100 can have a plurality of handle attachment sites 102, 104, 106, 108 so that the user can attach the handle 105 at any site to provide the most convenient access to the aperture and facilitate immobilization of other arteries. The handle can alternatively be positioned between the two cords at an orthogonal angle relative to the aperture axis and extending above the top surface of the base.

Figure 9:
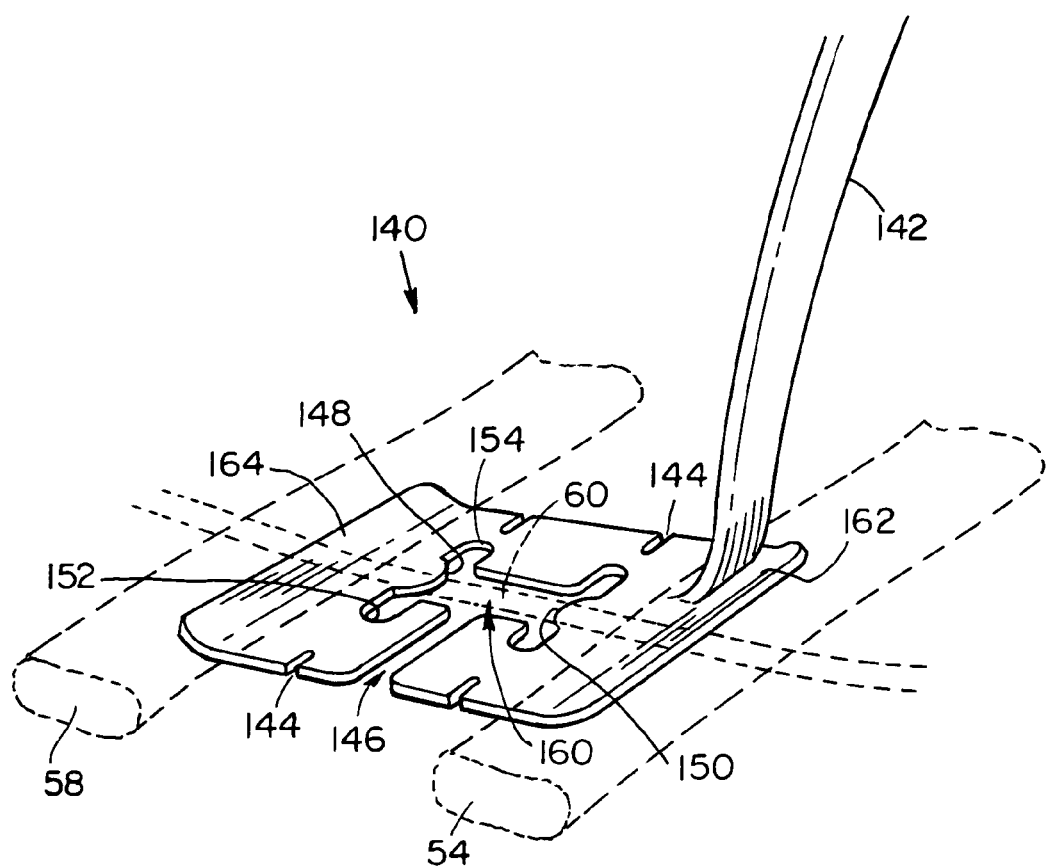
FIG. 9 is a top perspective view of another preferred embodiment of a surgical retractor in accordance with the invention.

In another preferred embodiment of the invention illustrated in the perspective view of FIG. 9, a retractor 140 has a handle 142, slots 144 located in the plane of the aperture 160 to secure the cords extending through lateral sections of the aperture (for example, sections 152, 154), end sections 162, 164 that engage the ribs 54, 58, tabs 148, 150 for compression of both sides of the artery at the site 60 and a side opening 146 so that the retractor can be removed.

In this embodiment, the LIMA slides out through opening 146 during removal of the retractor after completion of the procedure. This unitary retractor structure 140 can also include various features described previously in connection with the embodiment of FIG. 1 including the attached or integrated suction tube, the detachable handle, the irrigation or suction channel with ports or the mechanically actuated fasteners.

Figure 10:
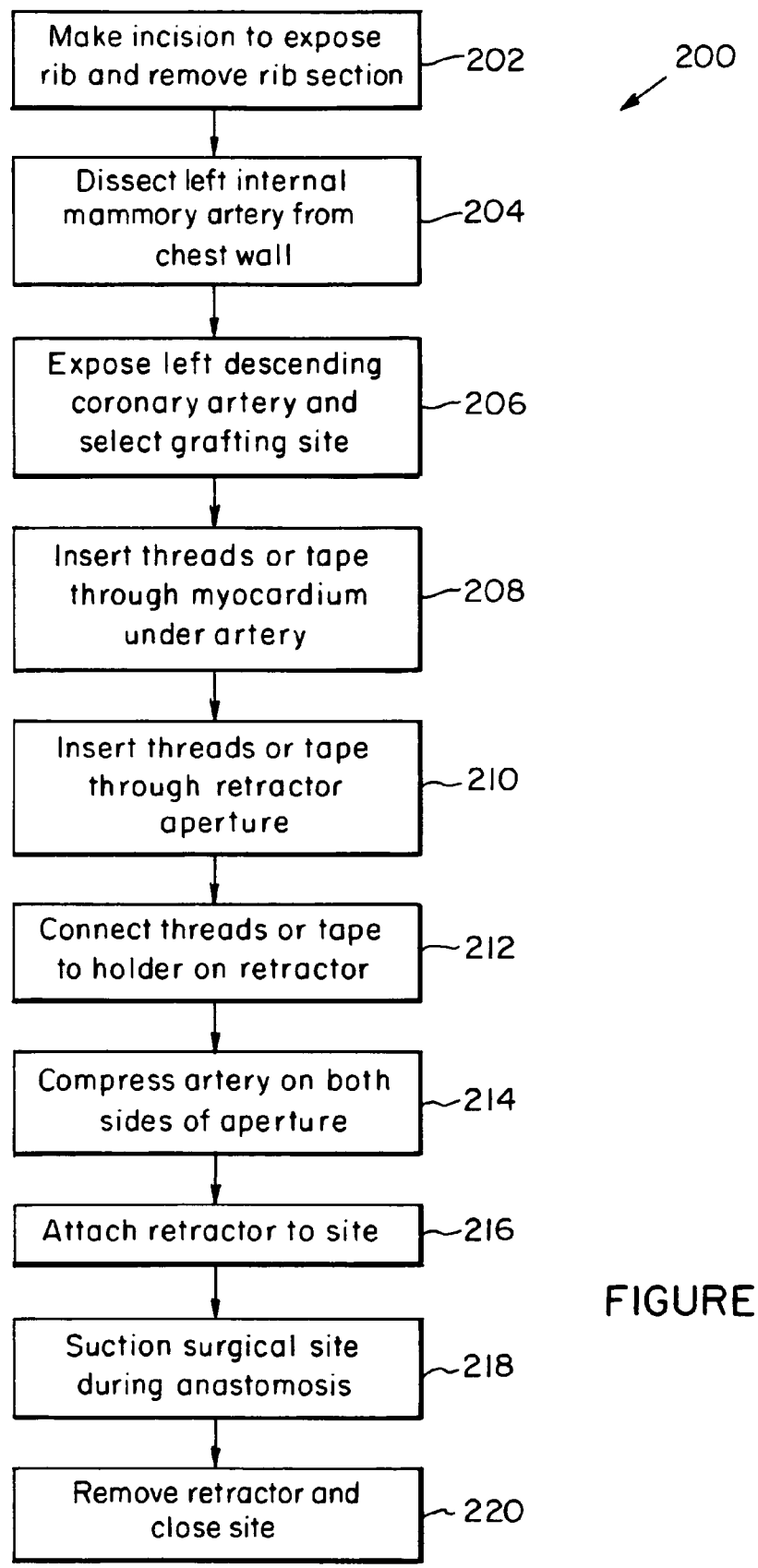
FIG. 10 is a schematic diagram illustrating a surgical procedure in accordance with the invention.

A preferred method of stabilizing tissue during a coronary bypass procedure 200 is illustrated in the process flow sequence of FIG. 10. A 5-8 cm sized incision is made over the 4th rib and a section of the 4th costal cartilage is removed 202. The LIMA is dissected from the chest wall 204 and divided distally. After blood flow assessment the LIMA can be temporarily closed with a spring loaded clip.

A self-retaining wound retractor is used to distract the edges of the incision and a "trap door" incision is made in the pericardium and the cut edge sewn to the skin to pull the pericardial sack and heart anteriorly. The LAD is exposed and a site suitable for anastomosis is selected for grafting 206. Tapes are inserted in the myocardium with blunt needles approximately 1-2 cm apart 208 and the retractor is inserted 210 with the tapes being pulled through the aperture and positioned in the lateral sections thereof. The tapes are connected to the holder 212 to compress the artery 214 and occlude blood flow on both sides of the grafting site. The tension in the tapes can optionally be adjusted during the procedure to minimize blood loss at the site.

The retractor is secured 216 at the site by positioning one or both ends under adjoining ribs, or alternatively, attaching the handle or arm to the wound retractor or other implement. The grafting site undergoes less than 0.1 mm of movement in any direction during this example procedure.

The site is suctioned or irrigated 218 during anastomosis, the grafting site is inspected, the tapes are released from the holders, and the retractor is removed either by sliding the LIMA through a side opening in the retractor or detaching a section of the retractor to accommodate removal of the LIMA from the aperture. After blood flow is restored, the site is inspected and closed 220.

Although the use of the retractor has been described in connection with a particular bypass procedure, it can also be used in other procedures such as bypass operations involving the diagonal, right or other coronary artery where movement at the site can interfere with the procedure.

Alternative embodiments involve opening of the chest and positioning the retractor at any exposed site on the heart wall or surrounding areas to immobilize the operative site. The retractor serves to isolate the site and limits or stops motion at the site due to respiratory movement of the lungs or the pumping motion of the heart.

Figure 11:
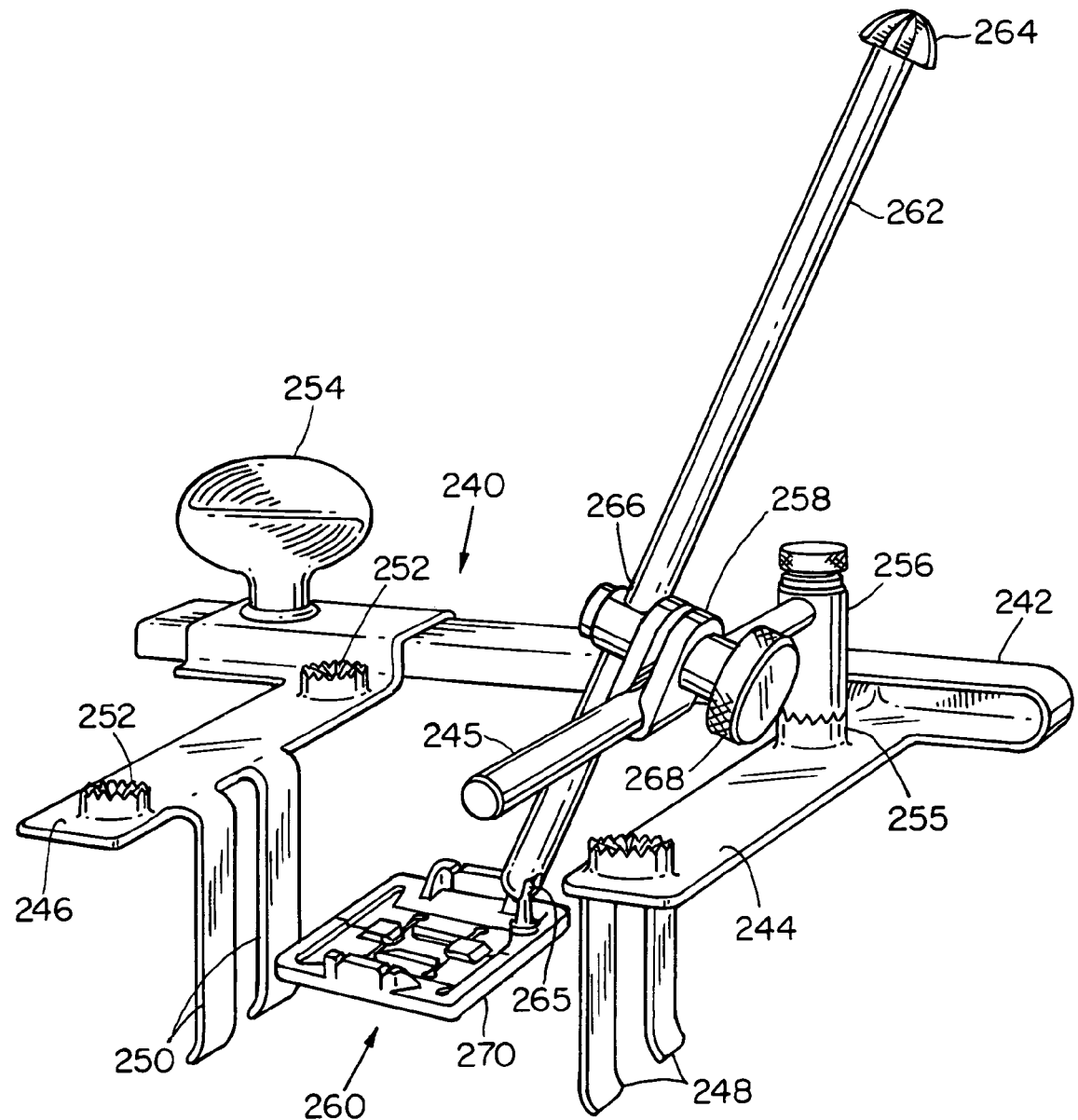
FIG. 11 is a perspective view of a frame supporting a retractor in accordance with the invention.

In another preferred embodiment, a stabilizer system or frame 240 manufactured by Genzyme Surgical Products is illustrated in FIG. 11 to support a surgical retractor 260 in accordance with the invention.

The frame 240 used with the invention includes a bar 242 having an arm 244 extending orthogonally from a first end and attached to a second arm 246 with a thumb screw at a second end. Each arm 244, 246 has a pair of mounting elements 252, 255 on which a pivot rod 256 can be mounted. This rod 256 can be rotated 360 degrees to any desired position such that mounting arm 245 can oriented relative to the surgical site as needed to position the retractor 260. Each arm 244, 246 has a pair of grippers 248, 250 that engage anatomical features such as neighboring ribs at the site to stabilize the frame 240.

Figure 12B:
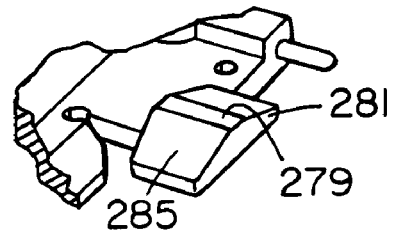
FIGS. 12A and 12B are enlarged detailed views of a surgical retractor in accordance with the invention.
Figure 12A:
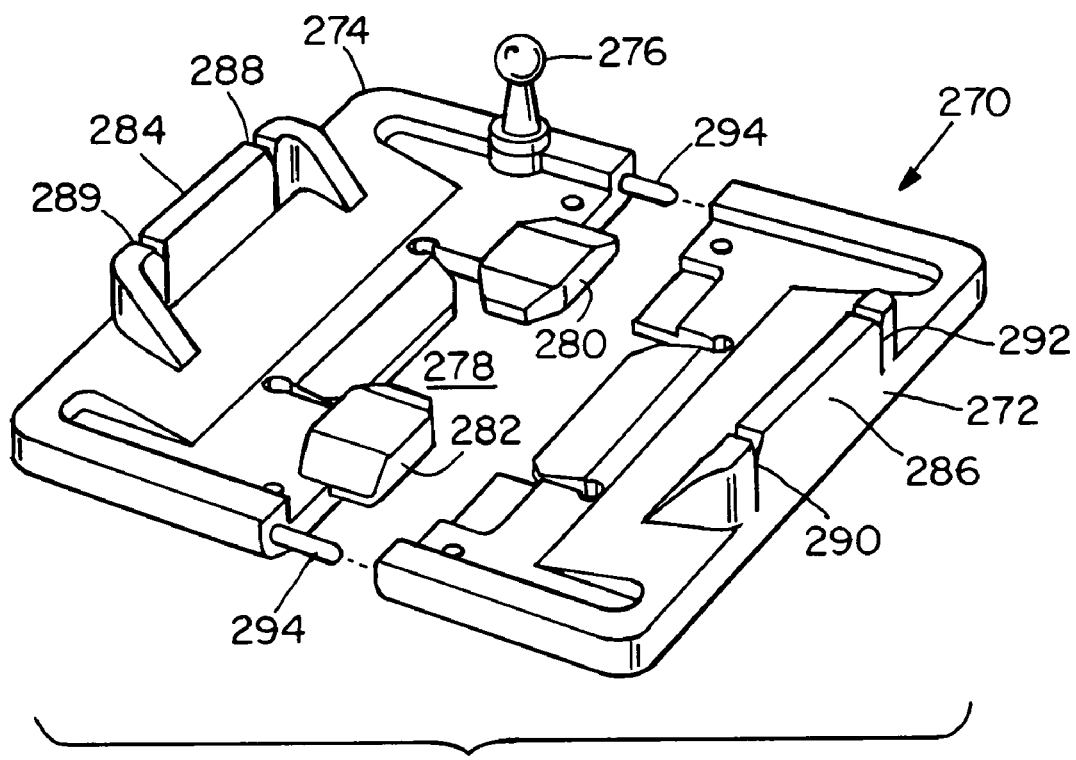

The mounting arm 245 supports the handle or support arm 262 with a friction fitting 258 which the user tightens with knob 268 to grip arm 262 at region 266. The support arm 262 has a knob 264 at one end that can be turned by the user to engage a post 276 shown in FIG. 12A. A ball on the post 276 can be slipped through an opening 265 in the second end of arm 262 and locked into position using knob 264.

The post 276 can be pivoted relative to arm 262 by loosening the knob 264, thus allowing the user to orient the retractor 260 at the site for fine positioning. The post 276 is mounted on a plastic retaining element 270 in this embodiment. The element 270 can be a transparent or opaque molded device that can be separated into two components 272, 274 as described previously. The two components can be attached by friction fit rods 294 that are inserted into holes in element 272. Element 270 can be made with a transparent material to enhance viability at the site.

Both components have raised holder elements 284, 286. Element 284 has a pair of slots 288, 289 that each frictionally grip an end of a cord which extends through the aperture 278 to attach tissue to the retractor. The second end of each cord is gripped by corresponding slots 290, 292 in element 286.

Tabs or cord retainers 280, 282 are integrally formed with component 274 and function as described previously. In the detailed partial view of FIG. 12B, the front inclined surface can be formed at a shallower angle such that the top ridge 279 is narrower. This embodiment of cord retainer 281 affords easier insertion of cords into the aperture.

This embodiment can also be formed with integral suction channels or openings in the top surface of the element 270. A suction tube can be attached through or with the arm 262 or attached to a suction port on element 270.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A surgical device for obstructing an artery during a coronary bypass procedure comprising:
    a retaining element having an aperture with at least four sides defining an operative site for formation of a graft with an artery;
    a connector;
    a holder on the retaining element, the holder including a first holder element and a second holder element that hold the connector on opposite sides of the aperture, the connector extending through the aperture and underneath a portion of the artery, the connector positioned by the holder opposite a compression surface of the retaining element, the holder holding the connector under tension to compress the artery between the connector and the compression surface, the connector and compression surface being positioned at a location to obstruct the artery during a coronary bypass procedure; and
    a handle that is attached to a mounting site on the retaining element.

2. The surgical device of claim 1 wherein the retaining element comprises a planar section surrounding the aperture.

3. The surgical device of claim 1 further comprising an irrigation channel in the retaining element.

4. The surgical device of claim 1 further comprising a post attached to the retaining element at the mounting site.

5. The surgical device of claim 1 wherein the aperture comprises a longitudinal section, a first lateral section and a second lateral section.

6. The surgical device claim 5 wherein the connector comprises a first cord, the first cord extending through the first lateral section, and a second cord extending through the second lateral section.

7. The surgical device of claim 6 wherein the cord comprises flexible tape or thread.

8. The surgical device of claim 1 wherein the retaining element comprises a compression surface that compresses an artery to control blood flow in the artery.

9. The surgical device of claim 8 wherein the compression surface comprises a tab defining an aperture sidewall.

10. The surgical device of claim 9 wherein the connector extends through a first section of the aperture and a second section of the aperture such that the tab is positioned between the first section and the second section.

11. The surgical device of claim 1 further comprising a suction tube that removes fluid on the retaining element.

12. The surgical device of claim 1 further comprising a connector such that the holder includes an opening that receives a portion of the connector.

13. The surgical device of claim 12 wherein the holder further comprises a second opening that receives a second portion of the connector.

14. The surgical device of claim 1 wherein the holder comprises a manually actuated fastener.

15. The surgical device of claim 1 wherein the retaining element comprises a plurality of separable sections.

16. The surgical device of claim 1 wherein the retaining element comprises a side opening in a base section extending into the aperture.

17. The surgical device of claim 4 further comprising a plurality of fluid openings in fluid communication with the channel.

18. A method of positioning an artery during surgery comprising the steps of:
    providing a retaining element attached to a handle, the retaining element having an aperture that exposes a portion of an artery at the surgical site;
    positioning the retaining element at a surgical site;
    positioning a connector between a first holder on the retaining element and a second holder on the retaining element, the connector extending underneath the artery; and
    occluding the artery at an arterial position of the surgical site with a surface of the retaining element extending along an axis above the connector.

19. The method of claim 18 further comprising connecting a flexible cord extending under the artery to the first holder and the second holder on the retaining element.

20. The method of claim 18 further comprising positioning a surface of the retaining element against an interior surface of a rib.

21. The method of claim 18 comprising the step of suctioning fluid from the surgical site with a suction tube attached to the retaining element.

22. The method of claim 18 wherein the connecting step further comprises attaching a cord extending through tissue to the first holder and the second holder on the retaining element.

23. The method of claim 18 further comprising providing a retaining element having a first plate and a second plate and removing the retaining element from the surgical site by separating the first plate from the second plate.

24. The method of claim 19 further comprising occluding the artery at the surgical site by pressing the artery against the retaining element with the flexible cord.

25. A surgical retractor comprising:
    a rigid retaining element having first and second sections, the first and second sections having an aperture with at least four sides such that the aperture is sized to allow the formation of a graft at a surgical site located within the at least four sides around the surgical site;
    said first and second sections being movable relative to each other to be removable from around the graft formed in said aperture; and
    a handle member removably attachable to said retaining element, said handle being oriented with respect to said retaining element to allow for the application of a tissue restraining force against the surgical site with said retaining element.

26. The surgical retractor of claim 25 further comprising tabs extending into the aperture.

27. The surgical retractor of claim 25 further comprising a plurality of stretchable cords removably attached to said retaining element wherein said cords are oriented with respect to said restraining element to allow for the application of a tissue restraining force against the surgical site adjacent to said aperture.

28. The surgical retractor of claim 25 further comprising a handle attachment site on the retaining element.

29. The surgical retractor of claim 25 further comprising a joint at a which the first and second sections are connected.

30. A method of positioning a surgical site during surgery comprising the steps of:
   positioning a rigid retaining element at the surgical site, the retaining element having first and second sections that form an aperture having at least four sides such that the aperture is sized to allow the formation of a graft therein;
   threading a plurality of cords through tissue surrounding the surgical site and removably element to position the surgical site with respect to the retaining element;
   performing a surgical procedure; and
   moving the first and second sections relative to each other to remove at least a portion of the retaining element from around the graft formed in the aperture.

31. The method of claim 30 further comprising providing a handle that is connected to the retaining element at a handle attachment.

32. The method of claim 30 further comprising occluding flow in an artery at the surgical site.

33. A method of positioning a surgical site during surgery comprising the steps of:
   positioning a rigid retaining element at the surgical site, the retaining element having first and second sections that form an aperture therebetween such that the aperture is sized to allow the formation of a graft therein;
   attaching a handle member to the retaining element to position the retaining element such that the surgical site is surrounded by at least four sides of the aperture;
   performing a surgical procedure; and
   moving the first and second sections relative to each other to remove at least a portion of the retaining element from around the graft performed in the aperture.

34. A method of positioning a surgical site during surgery comprising the steps of:
   positioning a rigid retaining element at the surgical site, the retaining element including an aperture that is sized to allow the formation of a graft therein;
   attaching a handle member to the retaining element to position the surgical site with respect to the retaining element and apply a downward retaining force to the surgical site with the retaining element;
   attaching a first cord under tension to the retaining element and attaching a second cord under tension to the retaining element to position the surgical site with respect to the retaining element to apply an upward retaining force to the surgical site against the retaining element at a first location with the first cord to obstruct an artery and at a second location with the second cord to obstruct an artery;
   performing a surgical procedure; and
   removing the retaining element from around the graft formed in the aperture.

35. A surgical device for obstructing an artery during a coronary bypass procedure comprising:
   a retaining element having an aperture with at least four sides defining an operative site for formation of a graft with an artery, the retaining element including a plurality of separable sections;
   a connector; and
   a holder on the retaining element, the holder positioned to hold the connector that extends through the aperture and underneath a portion of the artery, the holder aligning the connector with a compression surface of the retaining element such that the holder grips the connector under tension to compress the artery against the compression surface that is positioned at a location to obstruct the artery during a coronary bypass procedure.

* * * * *